(12) United States Patent
Sevenster et al.

(10) Patent No.: US 12,148,521 B2
(45) Date of Patent: Nov. 19, 2024

(54) CLOSED-LOOP RADIOLOGICAL FOLLOW-UP RECOMMENDATION SYSTEM

(71) Applicant: KONINKLIJKE PHILIPS N.V., Eindhoven (NL)

(72) Inventors: Merlijn Sevenster, Haarlem (NL); Sandeep Madhukar Dalal, Winchester, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1022 days.

(21) Appl. No.: 16/173,242

(22) Filed: Oct. 29, 2018

(65) Prior Publication Data

US 2019/0131011 A1    May 2, 2019

Related U.S. Application Data

(60) Provisional application No. 62/578,683, filed on Oct. 30, 2017.

(51) Int. Cl.
*G16H 30/20* (2018.01)
*G06F 16/9032* (2019.01)
*G16H 40/20* (2018.01)

(52) U.S. Cl.
CPC ....... *G16H 30/20* (2018.01); *G06F 16/90324* (2019.01); *G16H 40/20* (2018.01)

(58) Field of Classification Search
CPC .............................................. G06F 16/90324
See application file for complete search history.

(56) References Cited

U.S. PATENT DOCUMENTS

| 5,826,237 | A | * | 10/1998 | Macrae | G16H 40/63 707/999.1 |
| 7,966,195 | B2 | * | 6/2011 | Sanger | G06Q 10/00 705/2 |
| 8,285,565 | B2 | * | 10/2012 | Kerr | G16H 40/67 705/3 |
| 2004/0128164 | A1 | * | 7/2004 | DeJarnette | G06Q 30/04 705/2 |
| 2007/0271316 | A1 | * | 11/2007 | Hollebeek | G16H 30/20 |
| 2008/0255883 | A1 | * | 10/2008 | Jones | G16H 40/63 705/2 |
| 2010/0268547 | A1 | * | 10/2010 | DeJarnette | G16H 30/20 705/2 |

(Continued)

FOREIGN PATENT DOCUMENTS

WO    2017077501 A1    5/2017

*Primary Examiner* — Robert A Sorey

(57) ABSTRACT

A system (100) includes a processor (182) configured to generate (300) an unauthorized imaging order (122) for a patient from a follow-up recommendation for the patient. The unauthorized imaging order comprises a first anatomy, a first modality and/or a time interval. The processor is further configured to receive (320) an authorized imaging order (110) for the patient which includes a second anatomy and a second modality, and in response to an imaging examination of the patient according to the authorized imaging order and a determined overlap of the authorized imaging order and the unauthorized imaging order, acknowledge (360) that the follow-up recommendation has been satisfied by modifying a status of the unauthorized imaging order.

7 Claims, 3 Drawing Sheets

(56) References Cited

U.S. PATENT DOCUMENTS

| | | | |
|---|---|---|---|
| 2011/0010195 A1* | 1/2011 | Cohn | G16H 10/60 |
| | | | 705/3 |
| 2013/0188878 A1* | 7/2013 | Kacenjar | G06T 5/003 |
| | | | 382/209 |
| 2014/0200921 A1* | 7/2014 | Hamill | G16H 10/60 |
| | | | 705/3 |
| 2015/0149215 A1 | 5/2015 | Qian et al. | |
| 2017/0109473 A1* | 4/2017 | Kulon | G16Z 99/00 |
| 2018/0161010 A1* | 6/2018 | Choi | A61B 8/54 |
| 2020/0074118 A1* | 3/2020 | Sutton | G06F 16/2379 |
| 2020/0357505 A1* | 11/2020 | Szczykutowicz | G16H 50/70 |

\* cited by examiner

CLOSED-LOOP RADIOLOGICAL FOLLOW-UP RECOMMENDATION SYSTEM

FIELD OF THE INVENTION

The following generally relates to medical imaging and medical informatics and more particularly to a closed-loop radiological follow-up recommendation system, and is described with particular application to Computed Tomography (CT), but is also amendable to other imaging modalities, including Magnetic Resonance (MR), Positron Emission Tomography (PET), Single Proton Emission Computed Tomography (SPECT), Ultrasound (US), X-ray, combinations thereof, and/or other imaging modalities.

BACKGROUND OF THE INVENTION

An authorized medical imaging order for a patient is a medical imaging order prescribed by healthcare practitioner with authorization to prescribe the order for the patient such as a physician. Authorized medical imaging orders are typically entered into an order entry system by the ordering healthcare practitioner. The medical imaging order identifies a portion of a patient anatomy to be imaged, and an imaging modality, such as X-ray (CR, XA, RF), Mammography (MG), Computed Tomography (CT), Magnetic Resonance (MR), Positron Emission Tomography (PET), Single Proton Emission Computed Tomography (SPECT), Ultrasound (US), and combinations thereof.

Based on the entered order, an imaging examination for the patient is scheduled. A radiological healthcare practitioner, such as a radiologist, reviews the authorized medical imaging order and determines an imaging protocol. The review can include a search and/or a review of additional patient information, such as a completed patient questionnaire, a review of the electronic medical record (EMR), prior radiological reports, and combinations thereof. However, due to time constraints, the review of patient information is typically limited, and a strong reliance is often placed on a content of the authorized medical imaging order and any contraindications or complications screened through the patient questionnaire. For example, a patient questionnaire may screen for contraindications of certain contrast agents, e.g. diabetes, and/or medical device implants that may impact an imaging protocol selection.

The imaging protocol includes procedures for configuring the medical imaging device, which are to be performed in order to properly conduct the imaging examination and generate the expected diagnostic images. Selection of the protocol or "protocoling" is based on information gathered by the radiological healthcare practitioner subject to the time constraints. The protocol can include placement of fiducial markers, attachment of motion monitoring devices, contrast administration and monitoring, patient positioning and orientation, image acquisition parameters, image reconstruction parameters, image distribution procedures, and the like.

A radiological review of the generated image(s) may produce follow-up recommendations, such as incidental findings that cannot be diagnosed completely and therefore merit follow-up imaging. For example, in a review of a mammogram, a nodule in the adjacent lung tissue can be recorded as an incidental finding, and a follow-up recommendation is entered into a radiological report for the mammogram, which recommends a follow-up with a CT scan of the lung tissue within a three month time interval. Radiologists will typically describe the incidental finding to the best of their ability and provide a recommendation for follow-up.

Guidelines have been published on what are appropriate recommendations for certain finding types. Follow-up recommendations typically identify an anatomy to be imaged, a modality to image the anatomy, and a time interval within which the follow-up examination study is to be conducted. However, the radiology information technology (IT) infrastructure may not be capable of accurately managing follow-up recommendations. Unfortunately, this may lead to untimely diagnosis of incidental findings and/or additional ad hoc workflows executed by human agents "patching" the IT gap. The following are non-limiting examples of gaps and deficiencies:

Creation—Follow-up recommendations are provided in the radiology report in narrative form. The recommendations may be complete or incomplete (e.g., interval, modality and/or anatomy is lacking), but cannot directly be leveraged by downstream engines without a natural language processing engine that detects and normalizes them.

Monitoring—Follow-up recommendations are monitored by human agents. Dedicated administrative staff routinely checks recommendations that have not been acted upon and alerts responsible clinical staff.

Related Exam—The follow-up exam could potentially be combined with an exam acquired in the recommendation's time span. This may reduce imaging utilization, radiation dose and patient visits to the imaging facility. No mechanism is in place to monitor possible relationship between the follow-up exam and imaging done before.

Mission briefing—Upon loading the follow-up exam, the radiologist needs to acquaint himself with the patient's clinical history and the reason for this exam. Furnishing the radiologist with a comprehensive and actionable "mission briefing" is an important challenge in radiology informatics. In the context of a follow-up exam, this takes the form of bringing to the radiologist's attention the incidental finding and/or its earlier characterization in the report.

Closure—There is no step in which the radiologists acknowledges the follow-up recommendation and formally closes it during interpretation of the order. Such a step is required to ensure 100% follow-up compliance.

SUMMARY OF THE INVENTION

Aspects described herein address the above-referenced problems and others.

The following describes an embodiment(s) of a system(s), a method(s) and/or computer-readable storage medium(s) for compliance of radiological follow-up recommendations in a closed loop. An unauthorized imaging order is generated by a computer from electronic processing of a follow-up recommendation, which creates a loop. The follow-up recommendation can be obtained from a radiological report of the patient or directly entered by a radiological healthcare practitioner through a user interface. The unauthorized imaging order includes an anatomical portion of a patient to be imaged, an imaging modality, a recommended time interval, and combinations thereof. At the time of entry of an imaging order by a healthcare practitioner, the unauthorized imaging order can be ordered in combination with the imaging order. An imaging protocol is determined based on a combination of a received authorized imaging order by an ordering healthcare practitioner and the unauthorized imaging order. Compliance with the radiological follow-up recommendation can be acknowledged at the time of image protocol determination or during processing of the imaging report for the received authorized imaging order. The acknowledgement closes or terminates the loop.

In one aspect, a system includes a processor configured to generate an unauthorized imaging order for a patient from a follow-up recommendation in a radiological report of the patient. The unauthorized imaging order includes a first anatomy, a first modality, a time interval and combinations thereof. The processor is further configured to receive an authorized imaging order for the patient which includes a second anatomy and a second modality, and in response to an imaging examination of the patient according to the authorized imaging order and a determined overlap of the authorized imaging order and the unauthorized imaging order, acknowledge that the follow-up recommendation has been satisfied by modifying a status of the unauthorized imaging order.

In another aspect, a method includes generating an unauthorized imaging order for a patient from a follow-up recommendation in a radiological report of the patient using a configured processor. The unauthorized imaging order includes a first anatomy, a first modality, a time interval, and combinations thereof. An authorized imaging order is received for the patient, which includes a second anatomy and a second modality. In response to an imaging examination of the patient according to the authorized imaging order and a determined overlap of the authorized imaging order and the unauthorized imaging order, the follow-up recommendation that has been satisfied is acknowledged by modifying a status of the unauthorized imaging order.

In another aspect, a computer-readable storage medium carrying instructions controls one or more processors to generate an unauthorized imaging order for a patient from a follow-up recommendation in a radiological report of the patient. The unauthorized imaging order comprises a first anatomy, a first modality, a time interval, and combinations thereof. An authorized imaging order for the patient is received, which includes a second anatomy and a second modality. In response to an imaging examination of the patient according to the authorized imaging order and a determined overlap of the authorized imaging order and the unauthorized imaging order, the follow-up recommendation that has been satisfied is acknowledged by modifying a status of the unauthorized imaging order.

These and other aspects of the invention will be apparent from and elucidated with reference to the embodiment(s) described hereinafter.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
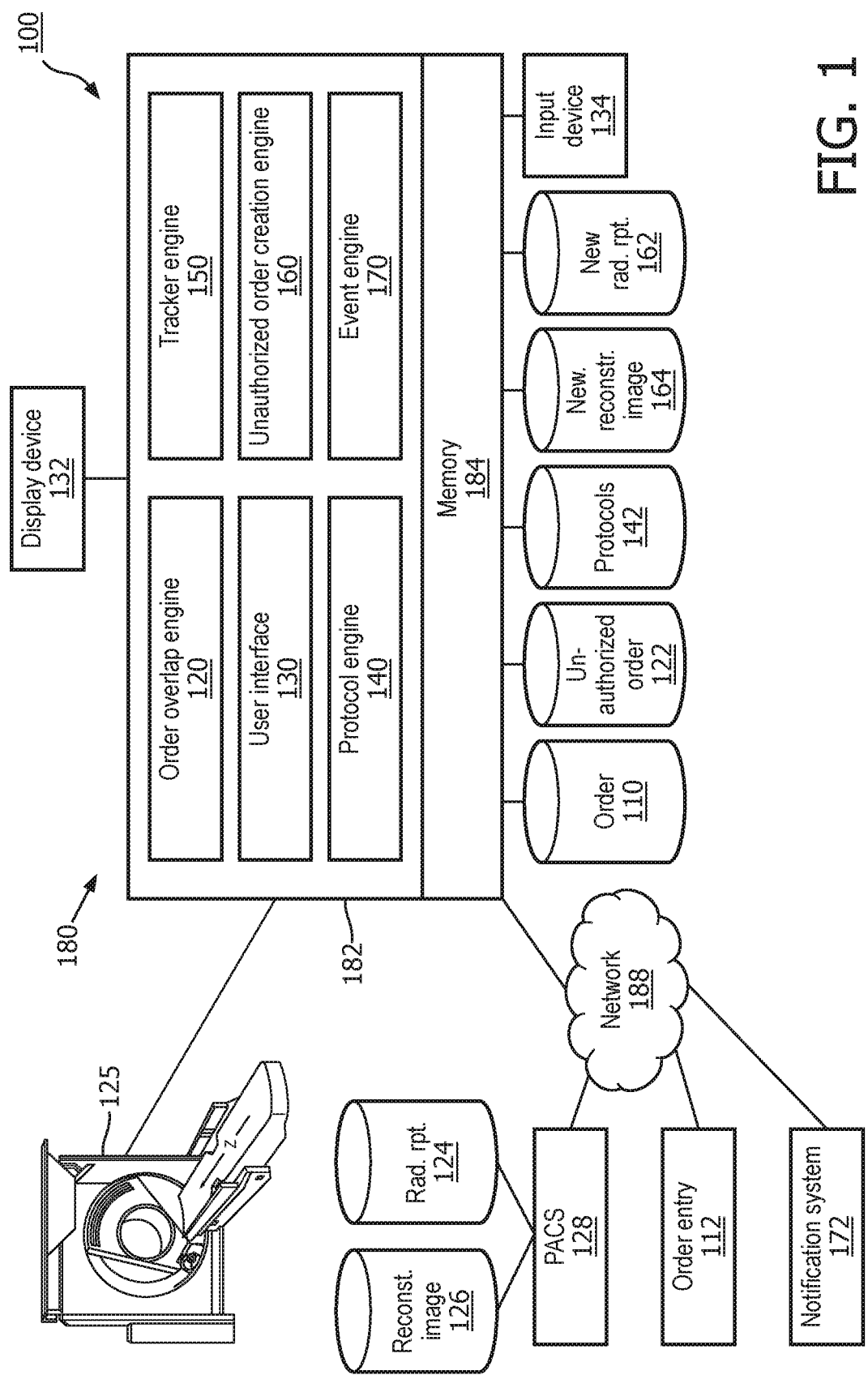
FIG. 1 schematically illustrates an embodiment of a closed loop system for promoting compliance with radiological follow-up recommendations.

With reference to FIG. 1, an embodiment of a system 100 configured for promoting closed loop compliance with a radiological follow-up recommendation(s) is schematically illustrated. An order 110 for an imaging examination for a patient is entered into an order entry system 112, such as by an ordering healthcare practitioner typing the order into a computing device (not shown) of the order entry system 112. The order 110 can include structured fields or unstructured prose in which an anatomy of the patient to be imaged and a modality are identified.

An order overlap engine 120 compares the entered order 110 from the order entry system 112 with an unauthorized order(s) 122 for the patient from a database of unauthorized orders. The order overlap engine 120 identifies an unauthorized order(s) 122 that overlaps the order 110 and can be combined with the order 110 into one ordered imaging examination. The unauthorized order 122 includes an anatomy, a modality, and a time interval for an imaging examination based on a follow-up recommendation from a prior radiological report 124 for the patient. In some embodiments, the unauthorized order 122 includes one or more links, such as a hyperlink, a pointer to a document name and location within the document, eXtended Markup Language (XML) reference, etc., to the prior radiological report 124 that includes the follow-up recommendation, which is the basis for the unauthorized order 122.

The comparison is based on the imaging modality and the anatomy present in the order 110 and also present in the unauthorized order 122. The order overlap engine 120 can normalize data in a structured order representing the anatomy and modality. Data normalization can include spelling correction, mapping of terms to a consistent lexicon, and reordering of terms. For example, CT, X-ray, computed tomography, CAT, computed aided tomography can be mapped to CT. The order overlap engine 120 can extract, identify and normalize data of the anatomy and the modality from the order 110 received in prose or narrative form using natural language processing (NLP) techniques, such as tokenization, lexicological and/or ontological mapping of terms to standard data values. For example, ontological mapping using Radlex® Playbook includes hierarchical groups of anatomies, where a liver is grouped and hierarchically mapped at a next higher level to an abdomen, and thus the liver and the abdomen anatomies overlap.

The overlap can include imaging modality, common anatomy, adjacent anatomy, and combinations thereof. For example, an order for an X-ray scan of a hip overlaps with an unauthorized order of a CT scan of the abdomen. In some embodiments, the overlap of anatomy can be in a common spatial region, which would be in a same examination region of a medical imaging device 125, such as a CT scanner, a MR scanner, a PET scanner, a SPECT scanner, an US scanner, an X-ray scanner, and combinations thereof. In some embodiments, the overlap can include inclusive, adjacent or nearby anatomical regions, which may include additional movement of the patient relative to the examination region of the medical imaging device 125. In some embodiments, the order overlap engine uses a set of rules to determine overlap. For example, a rule can include "if the anatomy of the unauthorized order is contained in the anatomy of the order using no more one hierarchical level of anatomy, and the anatomies match, then the order and the unauthorized order overlap." In some embodiments, the rules can include other factors of overlap, such as the time interval, a lesion type, and combinations thereof. The rules used in determining the overlap can use other factors whether or not present in the order 110 or the unauthorized order 122.

A user interface 130 can present, on a display device 132, the unauthorized order 122, which overlaps the entered order 110. In some embodiments, the entered order 110 is modified to include the overlapping unauthorized order 122. In some embodiments, the unauthorized order 122 is converted to a second entered order, which is linked to the entered order 110. For example, the unauthorized order 122 is converted to an authorized order in the order entry system 112, and electronic pointers are added to the original order and the second order to crosslink the two orders. In some embodiments, the unauthorized order 122 is identified as ordered when approved for inclusion in the combined imaging examination. In some embodiments, the user interface 130 is part of the order entry system 112. For example, the unauthorized order 122 is presented as a pop-up window for the order entry system 112. In some embodiments, the user interface 130 is separate and distinct from the order entry system 112. In some instances, the presentation of the unauthorized order 122 provides an additional notice to an ordering healthcare practitioner. That is, the presentation of the unauthorized order 122 acts in a push mode to provide notification of the follow-up recommendation, where reliance on the follow-up recommendation in the radiological report operates in a pull mode.

A protocol engine 140, based on an input from the input device 134, assigns the order 110 and the unauthorized order 122 to one or more protocols 142 for the single schedule imaging examination. In some embodiments, the anatomies of the ontology are further mapped to imaging protocols 142 and/or the protocols 142 are indexed by anatomy. The user interface 130 can present a list of the protocols 142 with the presentation of the order 110 and the unauthorized order 122. The list of the protocols 142 can be ordered and/or a subset of the protocols 142 presented according to the modality and the anatomy of the order 110 and the modality and the anatomy of the unauthorized order 122. In some instances, the presentation of the unauthorized order 122 provides additional notice to the radiological healthcare practitioner responsible for protocoling. That is, the presentation acts as a push mode to promote compliance with the corresponding follow-up recommendation.

In some embodiments, the radiological healthcare practitioner may need authorization from the ordering healthcare practitioner according to institutional and/or legal requirements to modify the order 110 and/or include the unauthorized order 122.

A tracker engine 150 prepares information for presentation that provides the basis for the unauthorized order 122. In some embodiments, the tracker engine 150 prepares narrative excerpts from the prior radiation report 124. For example, the sentence which includes the follow-up recommendation, the surrounding paragraph, a fixed number of surrounding sentences, sentences which specify the anatomy, the modality, and the time interval information as the basis for the unauthorized order 122, and combinations thereof can be formatted for presentation.

In some embodiments, the tracker engine 150 opens an image viewer with the prior image 126 location of an indicated finding presented in a view that is a basis for the follow-up recommendation and consequently for the unauthorized order 122. For example, an incidental finding of a nodule in an image slice is identified by an arrow in a Digital Imaging and Communications in Medicine (DICOM) viewer display.

In some embodiments, the user interface 130, in response to an input from an input device 134, presents the information prepared by the tracker engine 150, such as the narrative excepts of the prior radiological report 124, the finding in the prior image 126 or combinations thereof, which correspond to the unauthorized order 122. In some instances, the link(s) included in the unauthorized order provide fast and efficient access to the follow-up recommendation, report findings, or prior images 126. The prior radiological reports 124 and prior images 126 can be stored in a database or storage system 128, such as a Picture Archiving and Communication System (PACS), Radiological Information System (RIS), Electronic Medical Record (EMR), Hospital Information System (HIS) and the like.

The tracker engine 150 tracks the unauthorized order 122. The tracking can include recording an acknowledgement for the unauthorized order 122, which indicates compliance with the follow-up recommendation. The recorded acknowledgement can be stored with the unauthorized order 122. The user interface 130 can further provide modification and/or deletion of the unauthorized order 122. In some instances, the information prepared and presented provides for more efficient briefing of the radiological healthcare practitioner. For example, rather than having to pull information based on search and query of reports and/or images as part of the review of patient information, the prepared information can be provided in a focused and push mode.

An unauthorized order creation engine 160 identifies and extracts a follow-up recommendation and generates the unauthorized order 122 based on the follow-up recommendation. The unauthorized order 122 includes an anatomy to be imaged, a modality, and a time interval for the follow-up imaging examination. In some embodiments, the unauthorized order creation engine 160 identifies and extracts the follow-up recommendation from a narrative of a new radiological report 162. For example, using natural language processing (NPL) techniques, the new radiological report 162 is tokenized and segmented into sections, paragraphs and sentences. Keyword searches within sections identify the recommendation, such as keyword stemming of "recommend," which can be further clarified through lexicological and ontological interpretations.

In some embodiments, anatomies and modalities can be inferred from the context of the imaging examination of the new radiological report 162 and/or new radiological image 164, such as DICOM metadata. For example, an annotation marks an incidental finding, and the metadata includes the annotation. The metadata can include complex information, such as a slice and an anatomical location on the image, morphological attributes of the finding including size, margins, opacity, etc. The metadata can be structured in a complex data structure compliant with the Annotation Image Markup (AIM) standard. The metadata can include the follow-up recommendation data elements entered directly by the radiologist through the user interface 130 or a user interface overlaying the radiological image. The user interface for annotations or entry of the data elements can include point and click navigation, dictation, and combinations thereof.

In some embodiments, the follow-up recommendation is obtained from a dedicated panel. For example, the radiological healthcare practitioner reading the new radiological image 164 "flags" the imaging examination for follow-up in a workflow interactive with the PACS 128. A panel or displayed screen from the workflow can include data entry fields that provide entry or indication of the follow-up recommendation or data elements of the follow-up recommendation.

In some embodiments, information absent from the recommendation can be prompted for by the user interface 130. That is, initially the unauthorized order 122 may be incomplete or not include all of the anatomy to be imaged, the modality and the time interval. In some embodiments, the recommendation is entered through the user interface 130 and can include structured fields for the anatomy, the modality and the time interval.

In some embodiments, the unauthorized order creation engine 160 can include links to the narrative portions of the new radiological report and/or include the excerpted portions directly into the unauthorized order 122. In some embodiments, unauthorized order creation engine can include links to the image data, meta-data and/or image annotations. For example, the unauthorized order 122 can include an image identifier, slice identifier, meta-data field identifier, annotation identifier, and the like. The annotation identifier can be compliant with the Annotation Image Markup (AIM) standard.

An event engine 170 reviews outstanding unauthorized orders 122 and provides notice to responsible healthcare practitioners. The notice can be provided via a notification system 172, such as an email system, text message system, paging message system, and the like. The notice can include content or portions of the content of the unauthorized order 122, such as patient name and/or identifier, anatomy, imaging modality, time interval, follow-up recommendation, links to the radiological report 124, portions of the radiological report 124, links to the prior image 126, an image slice of the prior image 126 or a portion of the image slice, combinations thereof, and the like.

The order overlap engine 120, the protocol engine 140, the tracker engine 150, the unauthorized order creation engine 160, and the event engine 170 are suitably embodied by a configured computer processor 182, such as a digital processor, a microprocessor, an electronic processor, an optical processor, a multi-processor, a distribution of processors including peer-to-peer or cooperatively operating processors, client-server arrangement of processors over a network 188, and the like, and configured to compare the entered order 110 with unauthorized orders 122, and identify overlap between the order 110 and the unauthorized order 122, assign the order 110 and the unauthorized order 122 to one or more protocols 142, prepare information for presentation that provides the basis for the unauthorized order 122, track the unauthorized order 122, identify and extract a follow-up recommendation, generate the unauthorized order 122, review outstanding unauthorized orders 122, and provide notice.

The user interface 130 is suitably embodied by the configured processor 182, the display device 132, and the input device(s) 134, and the configured processor 182 is configured to operate the display device 132 and the input device 134.

The configured computer processor 182 executes at least one computer readable instruction stored in the computer readable storage medium 184 (which excludes transitory medium), such as an optical disk, a magnetic disk, semiconductor memory of a computing device with the configured processor 182, and/or other non-transitory medium to perform the disclosed techniques. The configured processor 182 may also execute one or more computer readable instructions carried by a carrier wave, a signal or other transitory medium. The lines between components in represented in the diagram of FIG. 1 represent communications paths.

The configured processor 182, the display device 132, and the input device(s) 134 can comprise a computing device 180, such as a console, a laptop computer, desktop computer, tablet computer, smartphone, body worn computing device, server, distributed or cooperative arrangement of computing devices, combinations thereof, and the like. The display device 132 is suitably embodied by a computer display, smartphone display, projector, body worn display, television (TV), combinations thereof, and the like. The input device 134 is suitably embodied by a keyboard, a mouse, a trackball, a microphone, combinations thereof, and the like.

The order 110, the unauthorized order 122, the protocol 142, the new reconstructed image 164 and the new radiology report 162 are suitably embodied by an electronic or computer memory, which can include data structures, file structures, database organization, image formats, and the like. The unauthorized order 122 is generated independent of the order 110. That is, a radiological healthcare practitioner cannot enter an authorized imaging examination order.

In some embodiments, the order overlap engine 120, the protocol engine 140, the tracker engine 150, the unauthorized order creation engine 160, and the event engine 170 are suitably embodied as computer program products.

Figure 2:
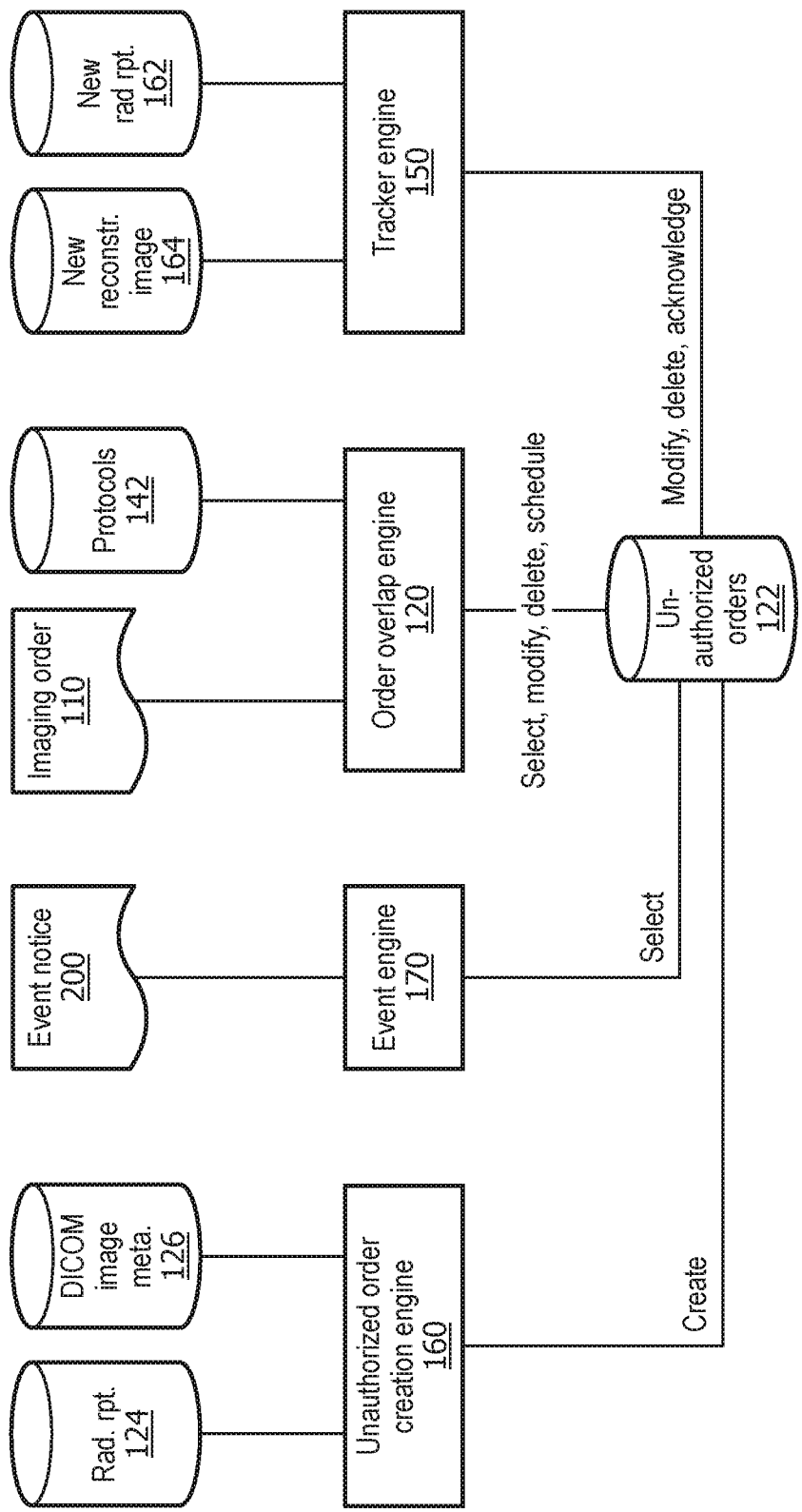
FIG. 2 schematically illustrates data flow in an embodiment of a closed loop system for promoting compliance with radiological follow-up recommendations.

With reference to FIG. 2, data flow in an embodiment of the closed loop system 100 is schematically illustrated. The unauthorized order creation engine 160 creates the unauthorized order 122 based on a follow-up recommendation in the radiology report 124. The unauthorized order 122 includes patient identifying information, a portion of anatomy to be imaged in a follow-up imaging examination, a modality for the imaging examination, and a time interval. The unauthorized order 122 can include ordering or referring healthcare practitioner information. The unauthorized order 122 can include links or excepted portions of the radiology report 124, links or excepted portions of the image data 126 including metadata, and combinations thereof. The content of the unauthorized order can obtained from the radiological report 124, the image data 126, directly from the radiological healthcare practitioner, and combinations thereof.

The event engine 170 according to a predetermined schedule selects the unauthorized orders 122 that are open, and generates event notices 200. The event notices 200 are generated for open unauthorized orders that are within a predetermined threshold of the time interval specified within the unauthorized order 122. For example, the threshold can include a fixed number of days or a percentage of days preceding or following the day set for the time interval. The time interval is a period of time according to the follow-up recommendation in which the recommended imaging study be conducted, such as 3 months or 90 days from the date of the radiological report 124. The event notice 200 can include a reference number or secured patient identifying information, the corresponding follow-up recommendation, the imaging modality, the anatomy, the time interval, links or excerpted portions of the radiological report 124, the prior image data 126, combinations thereof, and the like. The event notice 200 is sent or displayed electronically. For example, the event notice 200 can be displayed in a pop-up window on access of an electronic medical record (EMR) for a patient by the ordering healthcare practitioner. In another example, the event notice 200 can be sent as a message to the ordering healthcare practitioner via the notification system 172.

The order overlap engine 120 selects the unauthorized order 122 from the database or collection of unauthorized orders for comparison with the imaging order 110. The selection can be part of the initial order entry of the imaging order 110 by the ordering healthcare practitioner or part of the selection of the protocol 142 by the radiological healthcare practitioner. The order overlap engine 120 can modify, delete, or schedule the unauthorized order 122 in response to the determined overlap. For example, the order overlap engine 120 can combine the unauthorized order 122 into the imaging order 110 with input authorizing the change by the ordering healthcare practitioner and delete the unauthorized order 122. In another example, the order overlap engine 120 links the imaging order 110 to the unauthorized order 122 and modifies a status of the unauthorized order 122 from open to ordered.

The tracker engine 150, in response to a radiological interpretation, modifies, deletes or acknowledges the unauthorized order 122. The radiological interpretation can include review of the new reconstructed image 164 from the imaging examination, which satisfies the unauthorized order 122. The radiological interpretation can include preparation and/or analysis of the new radiological report 162 from the imaging examination, which satisfies the unauthorized order 122. For example, as in the tracker engine 150 receives an input according to a radiological healthcare practitioner reviewing the imaging examination conducted using the selected protocol 142 with the selected protocol 142 based on the combination of the order 110 and the unauthorized order 122. The tacker engine 150 changes the status of the unauthorized order 122 to acknowledged indicating compliance with the follow-up recommendation from which the unauthorized order 122 was created. The tracker engine 150 can further modify the unauthorized order 122 to include reference information of the new reconstructed image 164 and/or the new radiological report 162. Alternatively, the unauthorized order 122 can be deleted. In some instances, the changed status or modified unauthorized order with compliance information can be used to monitor and/or track compliance with follow-up recommendations.

Figure 3:
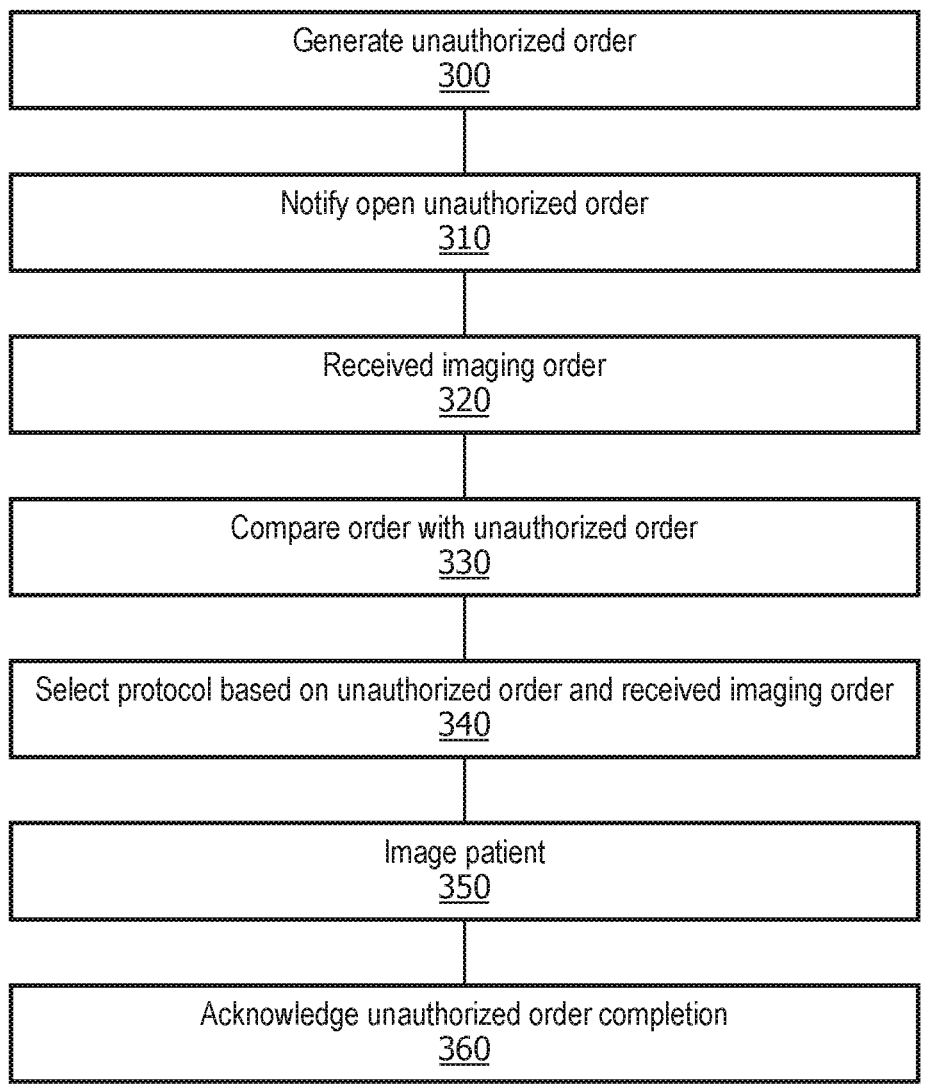
FIG. 3 illustrates a flowchart in accordance with an embodiment(s) herein.

FIG. 3 illustrates a flowchart in accordance with an embodiment(s) herein.

At 300, the unauthorized order 122 is generated according to the follow-up recommendation in the radiological report 124 of the imaging examination of the patient. The radiological report 124 interprets the image(s) 126 of the patient from the imaging examination. The unauthorized order 122 can be stored in a database of unauthorized orders.

At 310, the event notice 200 of an open status of the unauthorized order 122 is sent or delivered. The event notice 200 can be sent to the notification system 172. The identification and generation of the notification can include a periodic and/or scheduled query of the database of unauthorized orders. The notification can be refined to the unauthorized order 122, which is within a predetermined window of the time interval specified in each unauthorized order. In some instances, the unauthorized order 122 opens a loop that enables tracking of compliance with a follow-up recommendation from the radiological report 124, where conventional practice relies on the follow-up recommendation.

At 320, the imaging order 110 is received from the order entry system 112.

At 330, the unauthorized order 122 is selected, which overlaps with received imaging order 110. The selection can include the comparison of the order 110 and corresponding unauthorized orders 122 for the patient and further determined to overlap.

At 340, the protocol 142 is selected which satisfies the combination of the imaging order 110 and the unauthorized order 122. In some embodiments, the anatomies from the imaging order 110 and the unauthorized order 122 are imaged by the selected protocol 142. In some embodiments, the selected protocol(s) 142 can vary between the anatomy of the order 110 and the unauthorized order 122 by acquisition parameters, reconstruction parameters, presence or absence of a contrast agent, use of a motion or vital sign monitoring device, distribution parameters, combinations thereof and the like. For example, the protocol provides an imaging examination that includes a low dose CT scout of the lung anatomy from the unauthorized order 122, and a motion monitored CT scan with contrast of the heart anatomy from the imaging order 110. The heart anatomy and the lung anatomy overlap in the chest, and the modality of CT is common to the order 110 and the unauthorized order 122.

At 350, the imaging examination is performed according to the selected protocol 142, which is based on the combined imaging order 110 and the unauthorized order 122. The imaging examination generates the new reconstructed image(s) 164.

At 360, completion of the unauthorized order 122 is acknowledged based on the performed imaging examination. The acknowledgement can be included in the radiological interpretation, such as the presentation and review of the new reconstructed image 164, preparation and/or processing of the new radiological report 162, which interprets the new reconstructed image 164.

The above may be implemented by way of computer readable instructions, encoded or embedded on a computer readable storage medium, which, when executed by a computer processor(s), cause the processor(s) to carry out the described acts. Additionally or alternatively, at least one of the computer readable instructions is carried out by a signal, carrier wave or other transitory medium.

The above steps can be performed in a different order and/or some steps can be omitted.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with, or as part of other hardware, but may also be distributed in other forms, such as via the Internet or other wired or wireless telecommunication systems. Any reference signs in the claims should not be construed as limiting the scope.

The invention claimed is:

1. A method for imaging, comprising:
    processing, by a processor, a follow-up recommendation extracted by the processor from a radiological report;
    generating, by the processor, an unauthorized imaging order for a patient from the extracted follow-up recommendation based on the extracted follow-up recommendation, wherein the unauthorized imaging order comprises a first anatomy, a first modality and a time interval, and a status of the unauthorized imaging order is open;
    receiving, by the processor and from a computer memory, an authorized imaging order for the patient which includes a second anatomy and a second modality, wherein the authorized imaging order is entered by a healthcare practitioner with authorization to prescribe the authorized imaging order, and a status of the authorized imaging order is ordered;
    identifying the authorized imaging order overlaps the unauthorized imaging order based on overlap of the first and second anatomies and the first and second imaging modalities;
    selecting an imaging protocol that satisfies both the authorized imaging order and the unauthorized imaging order;
    linking the authorized imaging order to the unauthorized imaging order;
    modifying the status of the unauthorized imaging order to ordered; and
    performing an imaging examination according to the selected imaging protocol.

2. The method according to claim 1, extracting the follow-up recommendation from a radiological report for a previous imaging examination of the patient.

3. The method according to claim 1, further including:
    comparing at least the first anatomy and the first modality of the unauthorized imaging order with the second anatomy and the second modality of the authorized imaging order; and
    determining an overlap between the unauthorized imaging order and the authorized order based on a result of the comparing, wherein overlapping anatomy includes one of common anatomy, adjacent anatomy, or both common anatomy and adjacent anatomy.

4. The method according to claim 3, wherein the comparing comprises:
    determining whether the first anatomy is included in the second anatomy.

5. The method according to claim 1, further comprising:
    selecting an imaging protocol with imaging parameters for both the first anatomy of the unauthorized imaging order and the second anatomy of the authorized imaging order.

6. The method according to claim 2, further comprising:
    searching an electronic database for unauthorized orders that are open and within a predetermined threshold of the time interval, and sending an event notice for the unauthorized order within the predetermined threshold of a corresponding time interval.

7. The method according to claim 1, wherein generating the unauthorized imaging order includes:
    automatically identifying and extracting, with a processor, the follow-up recommendation by tokenizing and segmenting a report into sections, paragraphs and sentences, and keyword searching within the sections to identify the follow-up recommendation; and
    generating the unauthorized imaging order based on the follow-up recommendation.

* * * * *